US00PP23504P2

(12) United States Plant Patent
Dahlheimer et al.

(10) Patent No.: US PP23,504 P2
(45) Date of Patent: Mar. 26, 2013

(54) ***COREOPSIS* PLANT NAMED 'DAHL BABY'**

(50) Latin Name: ***Coreopsis* hybrid**
Varietal Denomination: Dahl Baby

(75) Inventors: Elizabeth Dahlheimer, Leola, PA (US); Robert Mark Saul, Atlanta, GA (US)

(73) Assignee: Aris Horticulture Inc., Barberton, OH (US)

( * ) Notice: Subject to any disclaimer, the term of this patent is extended or adjusted under 35 U.S.C. 154(b) by 0 days.

(21) Appl. No.: 13/507,576

(22) Filed: Jul. 11, 2012

(51) Int. Cl.
*A01H 5/00* (2006.01)

(52) U.S. Cl. ..... Plt./417

(58) Field of Classification Search ..... Plt./417
See application file for complete search history.

*Primary Examiner* — June Hwu
*Assistant Examiner* — Louanne Krawczewicz Myers
(74) *Attorney, Agent, or Firm* — Penny J. Aguirre

(57) ABSTRACT

A new cultivar of hybrid *Coreopsis* named 'Dahl Baby' characterized by its compact plant habit with a tight rosette of foliage, its abundance of bloom in spring, its 2.5 to 3.8 cm inflorescences comprised of golden yellow tubular ray florets surrounded golden disk florets, and its plant height of about 30 cm in bloom with a foliage height of 15 to 20 cm.

2 Drawing Sheets

Botanical classification: *Coreopsis* hybrid.
Variety denomination: 'Dahl Baby'.

BACKGROUND OF THE INVENTION

The present invention relates to a new and distinct cultivar of *Coreopsis* plant, botanically of hybrid origin and known as *Coreopsis* 'Dahl Baby' and will be referred to hereinafter by its cultivar name, 'Dahl Baby'. The new cultivar of *Coreopsis* is an herbaceous perennial grown for landscape and container use.

The new cultivar was discovered by one of the Inventors in July of 2008 as a naturally occurring whole plant mutation of *Coreopsis* 'Jethro Tull' (U.S. Plant Pat. No. 18,789) in a trial bed in Lancaster, Pa.

Asexual reproduction of the new cultivar was first accomplished by stem cuttings by one of the Inventors in Alpharetta, Ga. in September of 2008. The characteristics of this cultivar have been determined to be stable and are reproduced true to type in successive generations.

SUMMARY OF THE INVENTION

The following traits have been repeatedly observed and are determined to be the characteristics of the new cultivar. These attributes in combination distinguish 'Dahl Baby' as unique from all cultivars of *Coreopsis* known to the Inventors.

1. 'Dahl Baby' exhibits a compact plant habit with a tight rosette of foliage (typical of *C. auriculata*).
2. 'Dahl Baby' produces an abundance of bloom in spring; with an average of 300 inflorescences as grown in a one-gallon container.
3. 'Dahl Baby' exhibits 2.5 to 3.8 cm inflorescences comprised of golden yellow tubular ray florets surrounded golden disk florets.
4. 'Dahl Baby' reaches a height of 30 cm in height in bloom (foliage 15 to 20 cm in height) and 30 to 40 cm in width.

The parent plant of 'Dahl Baby', 'Jethro Tull' differs from 'Dahl Baby' in having tubular ray florets that are longer (25 cm versus 1.3 cm for 'Dahl Baby'), in having *C. lanceolata* type foliage (primarily lanceolate-shaped), and in being taller in height (foliage height of 30 to 40 cm versus 15 to 20 cm for 'Dahl Baby'). 'Dahl Baby' can be most closely compared to *Coreopsis auriculata* 'Zamfir' (not patented) and 'Nana' (not patented). 'Zamfir' differs from 'Dahl Baby' in having less ray florets, in having a less compact plant habit, and in having less uniform inflorescences. 'Nana' differs from 'Dahl Baby' in having ray florets that are flat (not fluted) and more golden in color, smaller disk diameter, in having broader foliage, in having a shorter spring bloom period, and in re-blooming if cut back after spring bloom ('Dahl Baby' produces only a few blooms if cut back after spring bloom).

BRIEF DESCRIPTION OF THE DRAWING

The accompanying colored photographs illustrate the overall appearance and distinct characteristics of the new *Coreopsis*. The photographs were taken of eight month-old plants of 'Dahl Baby' as grown in a one-gallon container in Lancaster, Pa.

The photograph in FIG. 1 provides a side view of 'Dahl Baby' in bloom.

Figure 1:
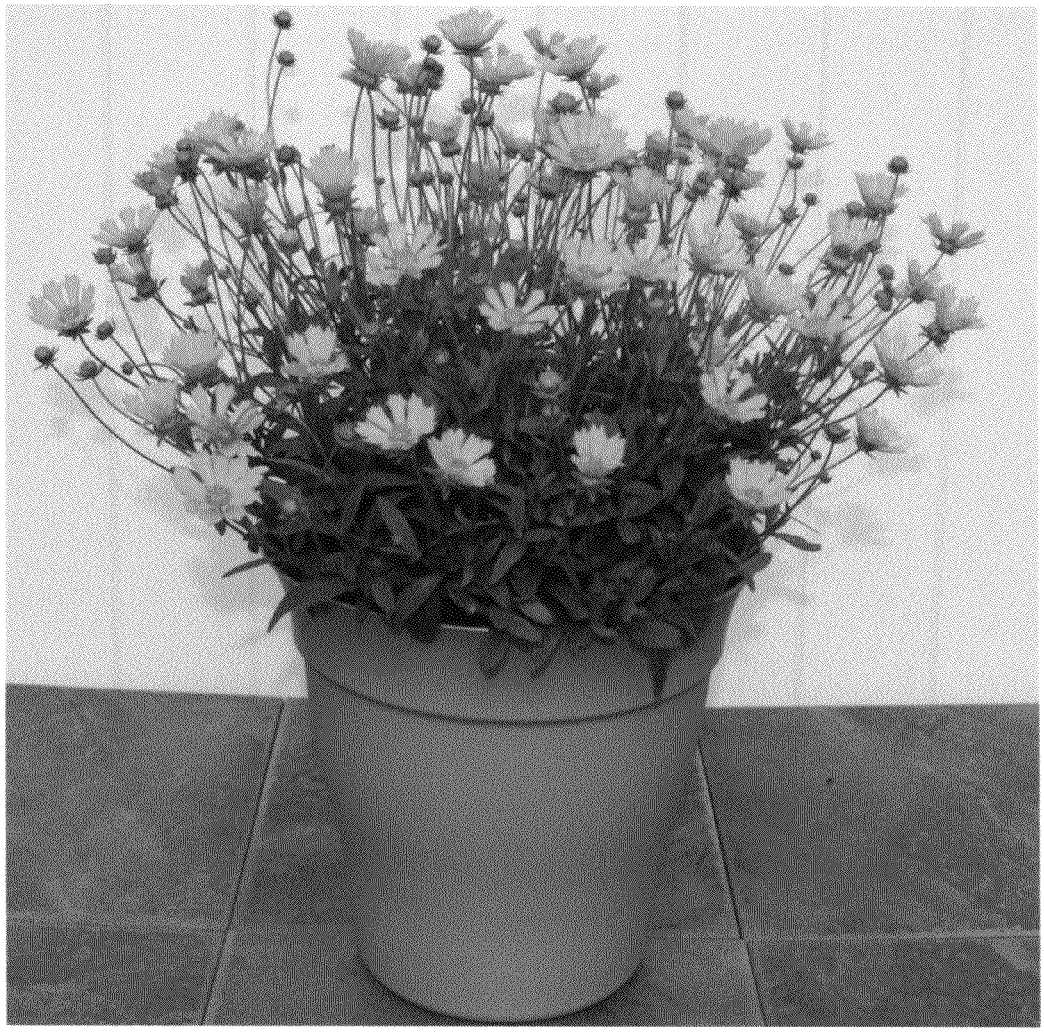
Figure 2:
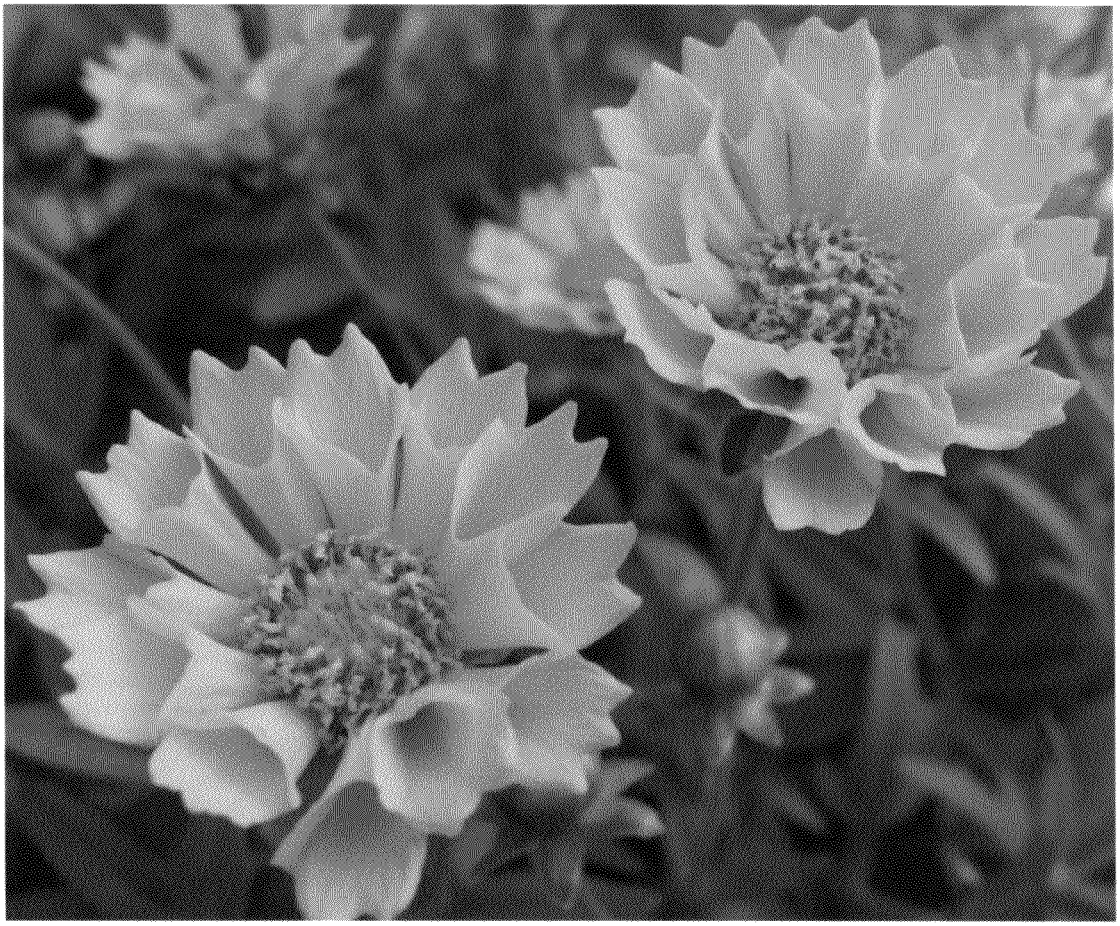

The photograph in FIG. 2 provides a close-up view of inflorescences of 'Dahl Baby'. The colors in the photograph may differ slightly from the color values cited in the detailed botanical description, which accurately describe the colors of the new *Coreopsis*.

DETAILED BOTANICAL DESCRIPTION

The following is a detailed description of 8 month-old plants of the new cultivar as grown in one-gallon containers in Lancaster, Pa. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Blooms from Mid April through June in Georgia and from mid May to the end of July in Pennsylvania.

*Plant habit*.—Herbaceous perennial, clump-forming, dense basal branching, sturdy stems.

*Height and spread*.—Reaches 30 cm in height in bloom (foliage 15 to 20 cm in height) and 30 to 40 cm in width.

*Hardiness*.—At least in U.S.D.A. Zones 5 to 8.

*Diseases resistance*.—No particular resistance or susceptibility to diseases was observed.

*Root description*.—Fibrous when young, becoming fleshy with age.

Growth and propagation:

*Propagation*.—Terminal stem cuttings.

*Growth rate*.—Moderate.

*Root initiation and development*.—14 days to initiate roots in a 70 to 70° F. greenhouse, a 72-cell plug is fully developed in 6 weeks, a 72-cell plug will finish in a 4-inch container in 3 to 4 weeks and a 1-gallon container in 6 to 7 weeks in a in spring.

Stem description:

*Shape*.—Rounded, solid, ridged.

*Stem color*.—144A.

*Stem size*.—An average of 23 cm in length (including terminal peduncle) and 4 mm in width.

*Stem surface*.—Pubescent with stiff hairs.

*Internode length*.—8 mm.

*Branching habit*.—An average of 50 basal branches, no lateral branches observed.

Foliage description:

*Leaf division*.—Simple.

*Leaf margins*.—Primarily trifid.

*Leaf size*.—Variable, an average of 7 cm in length and 4.5 cm in width.

*Leaf shape*.—Center lobes elliptic, side lobes lanceolate, linear base truncate at stem.

*Leaf base*.—Linear (about 35 cm in length) and truncate to stem.

*Leaf apex*.—Acute.

*Leaf venation*.—Pinnate, not prominent, mid rib upper surface 145C, mid rib on lower surface 146C.

*Leaf attachment*.—Sessile.

*Leaf arrangement*.—Opposite.

*Leaf surface*.—Puberulent on upper and lower surface.

*Leaf color*.—Young and mature upper surface; between 146A and N137A, young and mature lower surface; 147B.

Flower description:

*Inflorescence type*.—Composite with a single row of tubular ray florets surrounding disk florets in the center, forming a radiant head, inflorescences are borne on branch terminals in loose corymbs.

*Lastingness of inflorescence*.—About one week until senescence of ray florets, bracts and disk florets are persistent.

*Fragrance*.—None detected.

*Quantity of inflorescences*.—An average of 6 per branch, an average of 300 per plant grown in a one-gallon container.

*Inflorescence size*.—Corymbs; an average of 12 cm in width and height, composite; an average of 1.5 cm in depth and up to 3.2 cm in diameter with disk portion an average of 1.1 cm in diameter.

*Inflorescence buds*.—Average of 9 mm in depth and in diameter, shape is spherical, color; 7A (slightly greener) at apex surrounded inner 8 bracts 146A and outer bracts 137B.

*Peduncle*.—Corymb; an average of 6 cm in length and 2 mm in width, pubescent surface, 144A in color, composite; an average of 8 cm in length and 1.5 cm in width, 144A in color, surface primarily glabrous with a few sparse hairs.

Involucral bracts:

*Bract number*.—Two rows of 8.

*Bract arrangement*.—Outer bracts are un-fused and held slightly cupped upward, inner bracts surround receptacle with a campanulate form with apical portion un-fused, spreading, and held close to lower surface of ray florets.

*Bract size*.—Outer bracts; up to 7 mm in length and 3 mm in width, inner bracts; up to 1 cm in length and 4 mm in width with free portion an average of 7 mm in length and 4 mm in width.

*Bract color*.—Outer bracts; 146A on both surfaces, inner bracts; 146A on both surfaces with apex portion a blend of 137B and 151C.

*Bract texture*.—Glabrous on outer and inner bracts.

*Bract apex*.—Acute on outer and inner bracts.

*Bract base*.—Truncate on inner and outer bracts.

*Bract margins*.—Entire.

*Bract shape*.—Outer bracts; oblong, inner bracts; oblanceolate.

Ray florets (sterile):

*Number*.—An average of 11 arranged primarily in one row.

*Shape*.—Oblanceolate and tubular.

*Size*.—An average of 1.3 cm in length and 7 mm in width; with tube portion 1.5 cm in length.

*Apex*.—2 to 3 notched.

*Base*.—Cuneate.

*Margins*.—Entire with apex notched.

*Aspect*.—Held slightly upward from horizontal.

*Texture*.—Glabrous on inner and outer surfaces.

*Color*.—Inner and outer surface when opening and mature; 13A with slight veining of 144B (not conspicuous).

Disk florets (perfect):

*Shape*.—Tubular, corolla is fused, flared at apex.

*Number*.—About 150.

*Size*.—About 6 mm in length and 1.5 mm in width.

*Color*.—En masse; 17A, corolla; base of tube is 18B in color, flared portion is 17A and translucent.

*Receptacle*.—About 5 mm in diameter and 2 mm in depth, 146D in color.

Reproductive organs:

*Presence*.—Disk florets are perfect, ray florets are sterile.

*Gynoecium*.—1 Pistil, 6 mm in length, style is very fine and about 145D in color and translucent, bifid pilose stigma is 17A in color with branches about 0.7 mm in length and recurved, ovary is 1 mm in length, 0.5 mm in width, inferior, and 145D in color.

*Androcoecium*.—5 stamens, fused into tube surrounding style, 2 mm in length and 0.5 mm in width, about 200A in color, pollen is abundant and 17A in color.

*Fruit/seed*.—No fruit or seed development was observed.

It is claimed:

1. A new and distinct cultivar of *Coreopsis* plant named 'Dahl Baby' as herein illustrated and described.

* * * * *